(12) United States Patent
Knodel et al.

(10) Patent No.: US 8,469,253 B1
(45) Date of Patent: Jun. 25, 2013

(54) SURGICAL STAPLES ATTACHED TO RESORBABLE HOLDER

(75) Inventors: Bryan D. Knodel, Flagstaff, AZ (US); Bennie Thompson, Cincinnati, OH (US); Jinhoon Park, Palo Alto, CA (US); Nathan H. White, Redwood City, CA (US); Michael Murillo, Palo Alto, CA (US); Yaeer E. Lev, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 80 days.

(21) Appl. No.: 12/435,577

(22) Filed: May 5, 2009

(51) Int. Cl.
*A61B 17/064* (2006.01)

(52) U.S. Cl.
USPC .................................. 227/176.1; 227/175.1

(58) Field of Classification Search
USPC ..................................... 227/175.1–179.1, 19
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,899,914 A | 8/1975 | Akiyama |
| 4,086,926 A | 5/1978 | Green et al. |
| 4,228,895 A | 10/1980 | Larkin |
| 4,475,679 A | 10/1984 | Fleury, Jr. |
| 4,589,416 A | 5/1986 | Green |
| 4,633,861 A | 1/1987 | Chow et al. |
| 4,762,260 A | 8/1988 | Richards et al. |
| 4,969,591 A | 11/1990 | Richards et al. |
| 5,156,315 A | 10/1992 | Green et al. |
| 5,192,288 A | 3/1993 | Thompson et al. |
| 5,413,272 A | 5/1995 | Green et al. |

(Continued)

FOREIGN PATENT DOCUMENTS

| | | |
|---|---|---|
| EP | 1238634 | 9/1994 |
| JP | 2005160933 | 6/2005 |

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — M. Alexandra Elve
*Assistant Examiner* — Andrew M Tecco
(74) *Attorney, Agent, or Firm* — Cardica, Inc.

(57) ABSTRACT

One example of a surgical apparatus may include at least one resorbable feeder belt, and a plurality of staples fixed to that feeder belt. Another example of a surgical apparatus may include at least one feeder belt and at least one resorbable carrier detachably connected to a corresponding feeder belt, where the carrier includes a plurality of staples attached to it. An exemplary surgical method of treating tissue within the body of a patient may include providing a surgical instrument that includes an end effector moveable between an open configuration and a closed configuration, where the end effector includes an anvil and a staple holder pivotally connected to one another, where the anvil holds a knife; and at least one resorbable feeder belt and a plurality of staples fixed to the feeder belt, where the feeder belt extends into said staple holder; placing the end effector in proximity to tissue; deploying a plurality of staples into tissue; separating a distal segment of at least one feeder belt from a remainder of that feeder belt; and leaving that distal segment within the body of the patient.

19 Claims, 10 Drawing Sheets

U.S. PATENT DOCUMENTS

| | | | |
|---|---|---|---|
| 5,476,206 A | 12/1995 | Green | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,833,695 A * | 11/1998 | Yoon | 606/139 |
| 5,855,311 A | 1/1999 | Hamblin et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,843,403 B2 | 1/2005 | Whitman | |
| 7,025,747 B2 | 4/2006 | Smith | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,438,209 B1 * | 10/2008 | Hess et al. | 227/180.1 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering (124)*, (Jun. 2004),265-272.

Kolios, Efrossini et al., "Microlaparoscopy", *J. Endourology 18(9)*, (Nov. 2004),811-817.

Steichen, Felicien M., et al., "Mechanical Sutures in Surgery", *Brit. J. Surg. 60(3)*, (Mar. 1973),191-197.

Cardica, Inc., "Cardica Microcutter Implant Delivery Device 510(k)," Cover Sheet, Table 10.1, "Substantial Equivalence Comparison," and Section 12, "Substantial Equivalence Discussion," Oct. 18, 2010.

* cited by examiner

SURGICAL STAPLES ATTACHED TO RESORBABLE HOLDER

FIELD OF THE INVENTION

The invention generally relates to surgical staples and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient. Similar inconveniences may accompany the use of surgical staplers other than endocutters.

BRIEF DESCRIPTION OF THE DRAWINGS

The use of the same reference symbols in different figures indicates similar or identical items.

DETAILED DESCRIPTION

U.S. patent application Ser. No. 11/851,379, filed Sep. 6, 2007; U.S. patent application Ser. No. 11/956,988, filed Dec. 14, 2007; and U.S. patent application Ser. No. 12/263,171, filed Oct. 31, 2008 (the "Endocutter Applications") are hereby incorporated by reference herein in their entirety.

Figure 1:
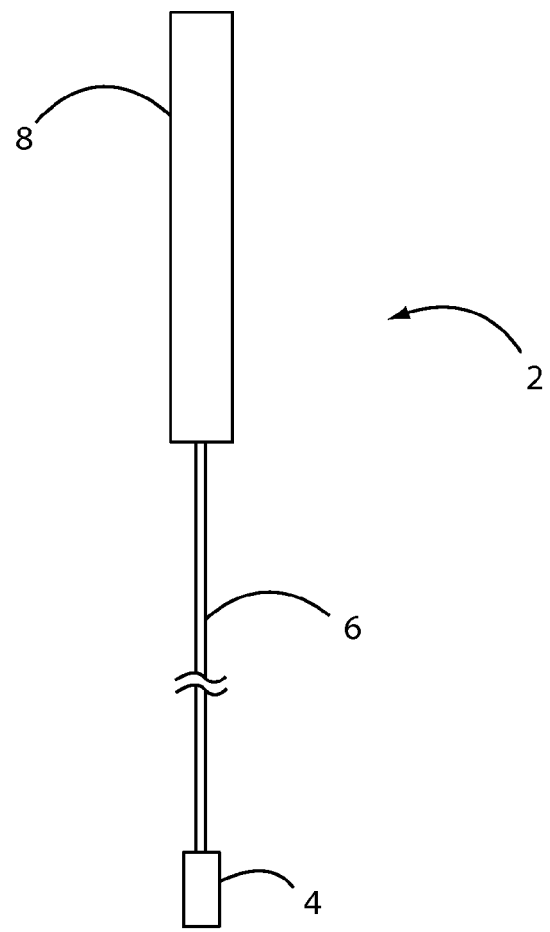
FIG. 1 is a schematic view of an endocutter.

The Endocutter Applications describe in detail examples of a true multi-fire endocutter. For example, referring to FIG. 1, an endocutter 2 includes an end effector 4 attached to a shaft 6, which in turn is attached to a handle 8. The end effector 4 may be one or more separate components that are connected to the shaft 6, or may be fabricated integrally with the distal end of the shaft 6. The shaft 6 of the endocutter 2 extends proximally from the end effector 4. The shaft 6 may be flexible or rigid. The shaft 6 may be articulated in at least one location, if desired. Optionally, the shaft 6 may include a cutaway, trough or other feature (not shown) to allow a guidewire (if any) or other positioning aid that may be used in the surgical procedure to remain in place during actuation of the endocutter 2. The end effector 4, shaft 6 and handle 8 may be substantially as described in the Endocutter Applications, unless otherwise described in this document.

Figure 2:
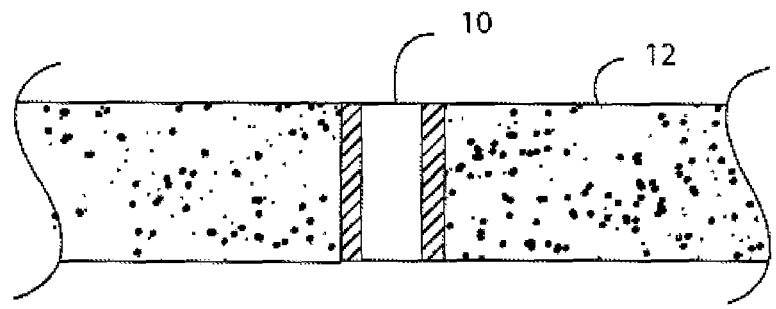
FIG. 2 is a cross-section view of a trocar port positioned in a patient.
Figure 3:
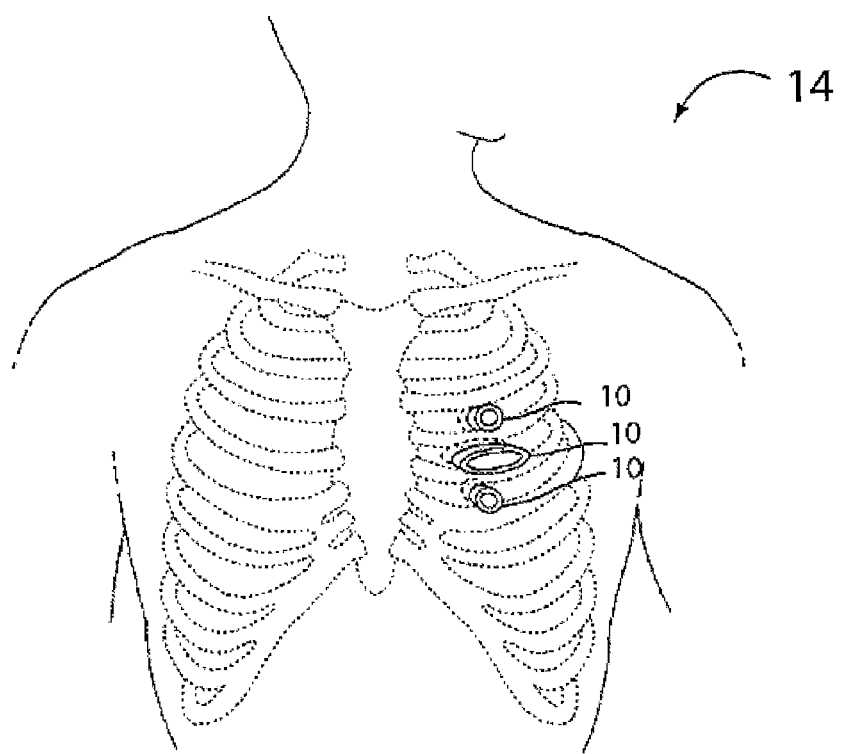
FIG. 3 is a cross-section view of trocar ports positioned in a patient.
Figure 4:
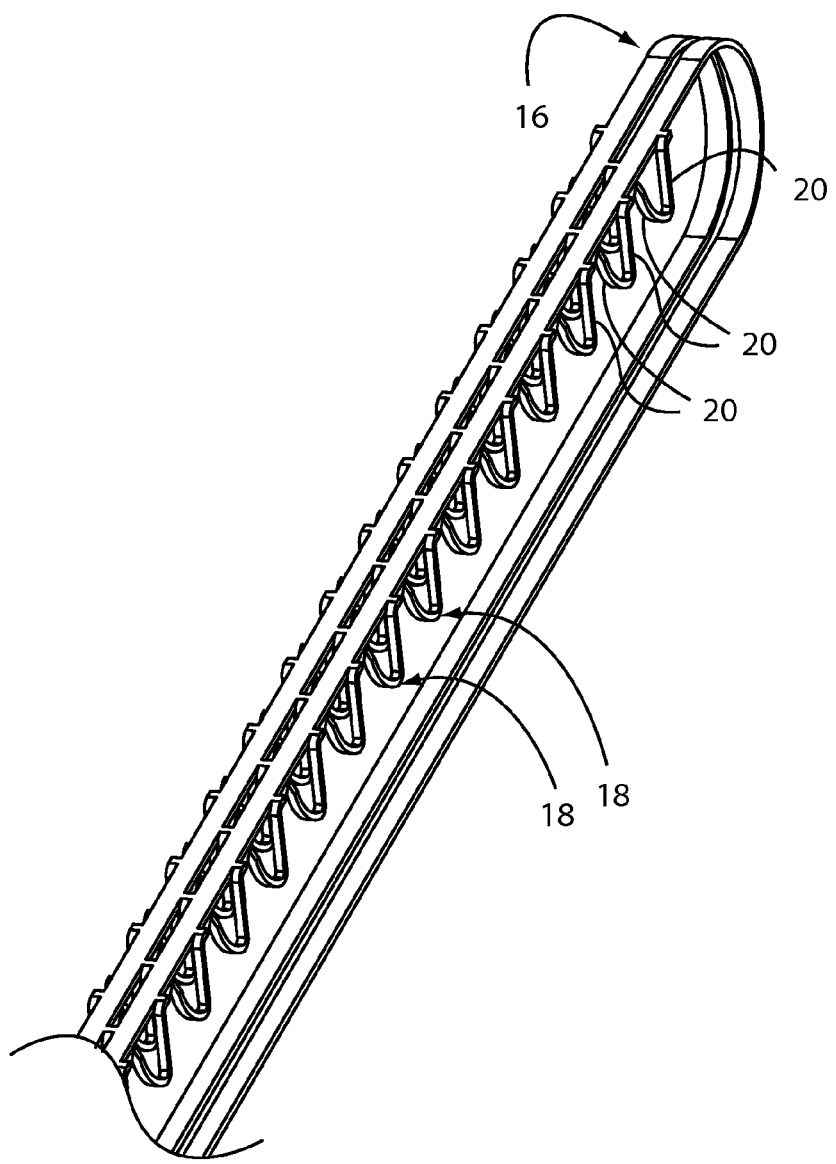
FIG. 4 is a perspective view of an exemplary feeder belt with three rows of staples frangibly connected thereto.

Referring also to FIGS. 2-3, the end effector 4 and the shaft 6 may be sized to pass through a standard trocar port 10 that may be placed through tissue 12 of a patient 14. Advantageously, the end effector 4 may be sized to pass through a trocar port 10 having an opening between 5-10 millimeters in diameter. Alternately, the endocutter 2 may be used in the course of conventional open surgery, where a trocar port is not used. Alternately, the endocutter 2 may be used in the course of minimally-invasive surgery, where access to the surgical site in the patient is gained through a mechanism or structure other than a trocar port, such as the LAP DISC® hand access device of Ethicon Endo-Surgery, Inc., or where access to the surgical site in the patient is gained through an incision or opening in which no port or other mechanism or structure is placed.

Figure 5:
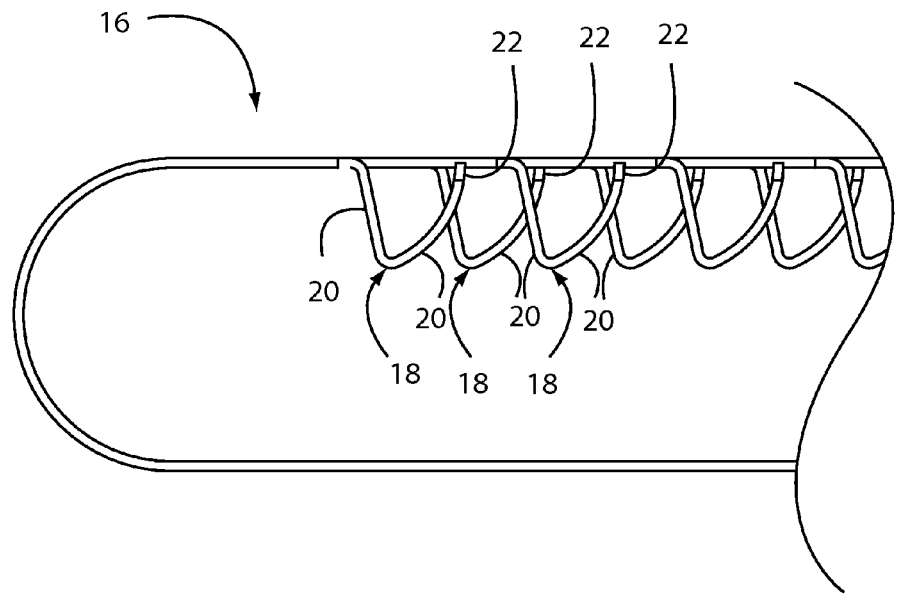
FIG. 5 is a side view of the feeder belt of FIG. 4.
Figure 6:
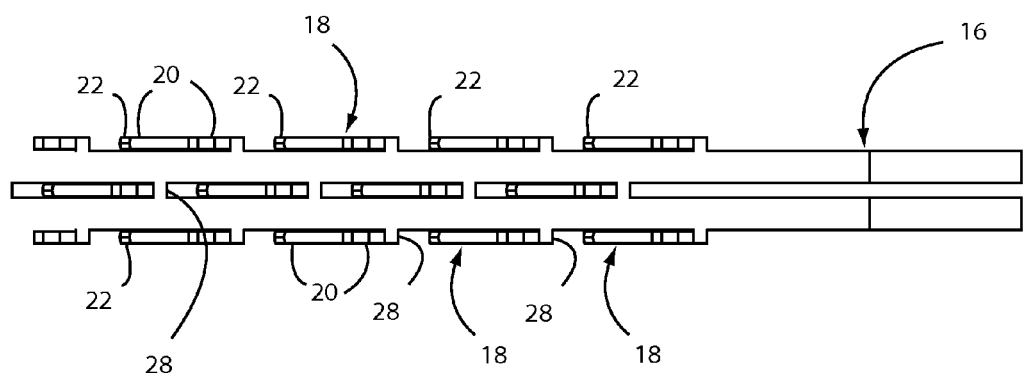
FIG. 6 is a top view of the feeder belt of FIG. 4.
Figure 7:
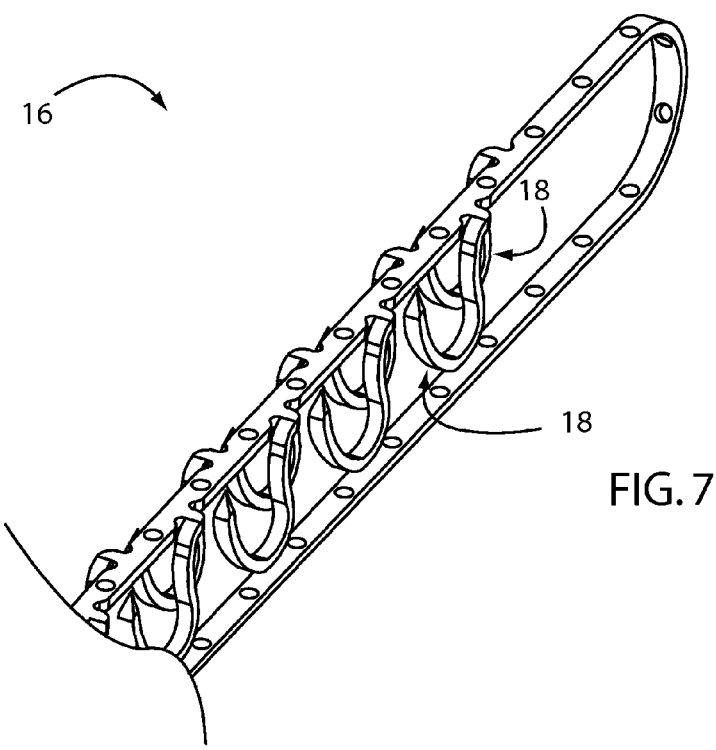
FIG. 7 is a perspective view of another exemplary feeder belt with two rows of staples frangibly connected thereto.
Figure 8:
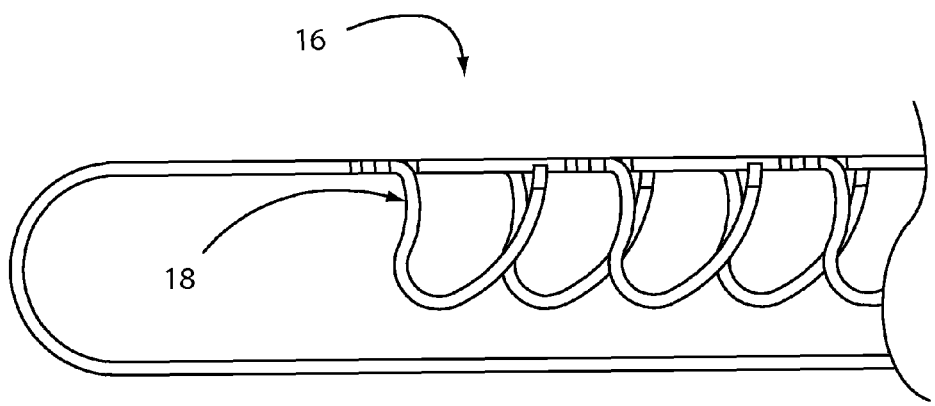
FIG. 8 is a side view of the feeder belt of FIG. 7.

Referring to FIGS. 4-9, a portion of an exemplary feeder belt 16 is positioned within the end effector 4. The feeder belt 16 and associated hardware may be as set forth in the Endocutter Applications. The feeder belt 16 may be a long, narrow, thin strip of material from which one or more staples 18 extend. The feeder belt 16 may be fabricated from stainless steel, nickel-titanium alloy, or any other suitable metallic or non-metallic material. The feeder belt 16 is flexible enough, and strong enough, to be advanced linearly and then redirected around a nose or other structure in substantially the opposite direction, as described in greater detail below. Alternately, at least part of the feeder belt 16 may be rigid or at least partially rigid, such that the feeder belt 16 may be advanced or retracted substantially linearly without redirection about a structure, or may be otherwise manipulated. Each staple 18 may be shaped in any suitable manner; the staples 18 may be shaped substantially the same as one another, or may be shaped differently. As one example, each staple 18 is generally V-shaped, and has two legs 20 extending from the base of the V-shape. Referring particularly to FIG. 5, one leg 20 of the staple 18 may be generally straight, and the other leg 20 of the staple 18 may be gently curved. However, the legs 20 may be shaped in a different manner. Further, each leg 20 may be shaped in the same manner. The staple 18 need not be symmetrical, but can be fabricated symmetrically if desired. The base of the V-shape of the staple 18 may be curved, pointed or otherwise configured. One leg 20 of the staple 18 has a free end 22 that may be characterized as a tissue penetrating tip 22. The tissue penetrating tip 22 may be sharpened, if desired, to facilitate penetration of tissue. However, the legs 20 of the staple 18 may have a cross-section that is small enough that the tissue penetrating tip 22 need not be sharpened in order to easily penetrate tissue. The other leg 20 is attached at one end to the feeder belt 16. Advantageously, that leg 20 is frangibly connected to the feeder belt 16. Thus, one end of the staple 18 may be attached to the feeder belt 16 and the other end of the staple 18 may be free. Alternately, the staple 18 may have three or more legs 20, or may be shaped in any other suitable manner. The staples 18 may be connected to the feeder belt 16 in any suitable orientation. As one example, one or more of the staples 18 are oriented generally parallel to the longitudinal centerline of the feeder belt 16. That is, one or more of the staples 18 each may lie in a plane that is generally parallel to the longitudinal centerline of the feeder belt 16, as shown in FIG. 6. As another example, one or more of the staples 18 each may be oriented in a direction angled relative to the longitudinal centerline of the feeder belt 16. As another example, the staples 18 each may be oriented in a direction angled relative to the transverse direction, which is the direction perpendicular to the longitudinal centerline of the feeder belt 16.

Figure 9:
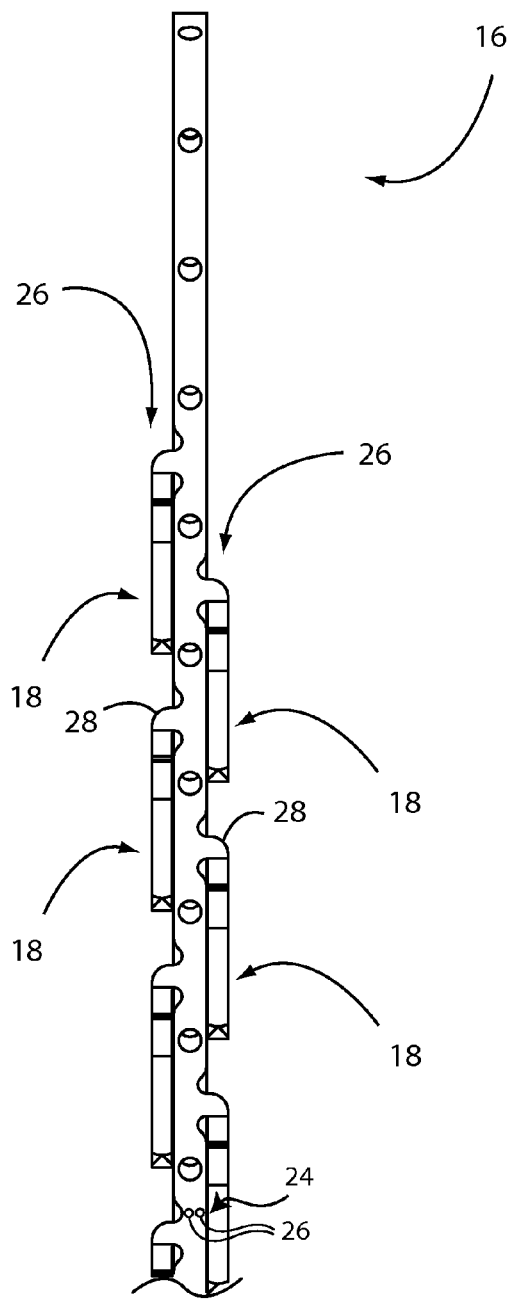
FIG. 9 is a top view of the feeder belt of FIG. 7.

The staples 18 may be arranged on a corresponding feeder belt 16 in any suitable manner, such as described in the Endocutter Applications. A connection between the feeder belt 16 and each corresponding staple 18 may be made in any suitable manner. That connection may be frangible or fixed. The Endocutter Applications describe a frangible connection between the feeder belt 16 and at least one staple 18. At least one staple 18 may be fixedly connected to the feeder belt 16, such that the staple 18 is retained on the feeder belt 16 after its deployment. Such a fixed connection may be accomplished in any suitable manner. As one example, a fixed connection between a staple 18 and the corresponding feeder belt 16 may be made in a similar manner as the frangible connection, where the weakened area at the junction between the staple 18 and the corresponding feeder belt 16 simply is omitted. As another example, a positively strengthened area may be provided at the junction between the staple 18 and the corresponding feeder belt 16. That strengthened area may be a wider and/or thicker leg 20 of the staple 18, at least in the vicinity of the junction between that leg 20 and the feeder belt 16. Such a strengthened area may instead, or additionally, be a differently-shaped and/or sized junction between the feeder belt 16 and the corresponding leg 20 of the staple 18 and the feeder belt 16, such that an increased cross-sectional area is present at the junction as compared to the cross-sectional area of such junction where a staple 18 is frangibly connected to the feeder belt 16. As another example, the strengthened area may also, or instead, be physically treated or otherwise configured to be stronger than the surrounding material, while having substantially the same physical dimensions as that surrounding material.

Where at least one staple 18 is fixedly connected to the feeder belt 16, the feeder belt 16 may be fabricated such that it remains in place in the body along with one or more staples 18. If so, the feeder belt 16 and the staple or staples 18 fixedly connected thereto may be fabricated from any biocompatible material which does not degrade substantially in the body, such as stainless steel or a titanium alloy.

Where at least one staple 18 is fixedly connected to the feeder belt 16, the feeder belt 16 may be fabricated such that it is resorbable. The staples 18 may also be configured to be resorbable, or may be fabricated to remain in place in the body after the feeder belt 16 has been resorbed. A resorbable feeder belt 16 may be fabricated from any suitable material that is resorbed by the body over time. Those suitable materials include, and are not limited to, polymers such as polydioxanone, polylactic acid and polyglycolic acid; polycarbonates such as poly(desaminotyrosyl-tyrosine-ethyl ester carbonate) (PDTE carbonate); polysaccharides such as starch/cellulose acetate blends, starch/polycaprolactone blends, and glucosaminoglycans; polyanhydrides such as aliphatic polyanhydrides or aromatic polyanhydrides; polyaminoacids such as poly-L-lysine; pseudo-polyaminoacids; and polyphosphazenes.

Where the feeder belt 16 and at least one staple 18 are made of different materials, the one or more staples 18 may be attached to the feeder belt 16 in any suitable manner. As one example, where the feeder belt 16 is resorbable and one or more staples 18 are not, the feeder belt 16 may be molded onto the one or more staples 18 that are non-resorbable. As another example, one or more staples 18 may be welded to the feeder belt 16, or attached to the feeder belt 16 with adhesive. As another example, one or more staples 18 may be attached to the feeder belt 16 by localized melting of the feeder belt 16 at the junction between at least one staple 18 and the feeder belt 16; as the feeder belt 16 cools, the junction hardens to form an attachment to one or more staples 18. Any other suitable structure, mechanism or method may be used to attach one or more staples 18 to a resorbable feeder belt 16. In a similar manner, or in any other suitable manner, the feeder belt 16 may be attached to a top plate and/or bottom plate, and/or any other suitable structure or mechanism, of the endocutter 2 that is utilized to advance the feeder belt 16.

Where the feeder belt 16 is resorbable, the feeder belt 16 itself and/or the end effector 4 of the endocutter 2 may be configured in any way to allow a portion of the feeder belt 16 to be deployed into the patient along with one or more staples 18 fixed thereto. Referring also to FIG. 9, at least one feeder belt 16 may include at least one perforation 24. Each perforation 24 may include one or more holes 26 defined partially or completely through the feeder belt 16. Where the perforation 24 includes two or more holes 26, the holes 26 may lie substantially along a straight line. That straight line may be oriented generally perpendicular to the longitudinal centerline of the feeder belt 16, or may form a different angle relative to the longitudinal centerline of the feeder belt 16. Alternately, the holes 26 of a perforation 24 may lie substantially along a curved line. Alternately, a perforation 24 may include at least one hole 26 that is not aligned with the other holes 26 along either a straight line or a curved line. Each perforation 24 is strong enough to allow for advancement of the feeder belt 16 in which it is defined, but weak enough to allow the section of the feeder belt 16 distal to the perforation 24 to detach from the remainder of the feeder belt 16. Optionally, the perforation 24 may be stronger in compression than in tension, to allow the feeder belt 16 to be pushed distally (during which the perforation 24 is in compression) and then separated from the remainder of the feeder belt 16 by the application of a tensile force. The end effector 4 may be configured to provide such a tensile force in any suitable manner. As another example, after the staples 18 are deployed into tissue such that they hold the distalmost section of the feeder belt 16 in place at a surgical site in the body, the feeder belt 16 may simply tear at the perforation 24 upon motion of the end effector 4 away from that surgical site.

Figure 10:
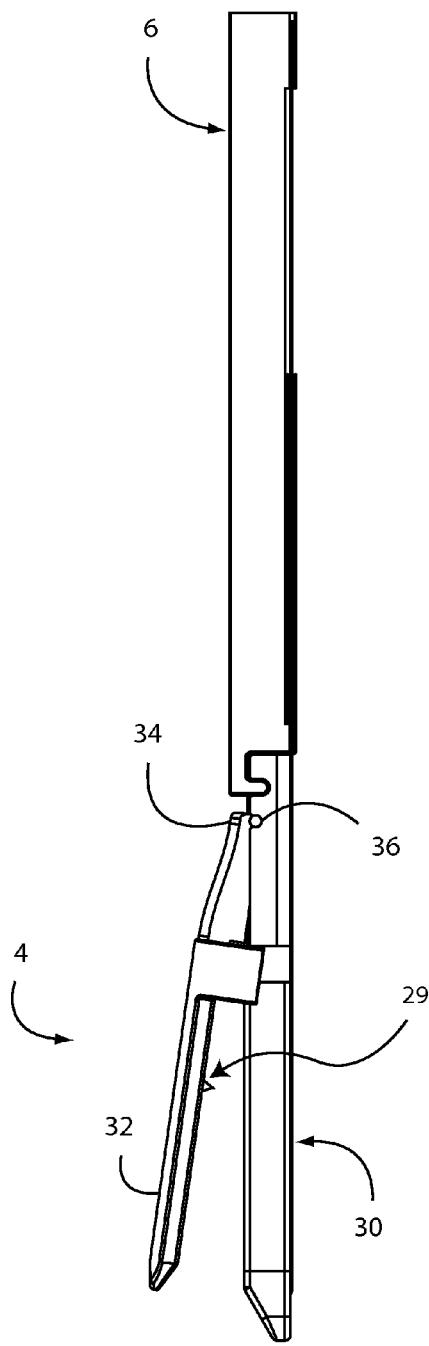
FIG. 10 is a side view of an exemplary end effector of an endocutter that utilizes the feeder belt of FIGS. 1-9.

As another example, referring also to FIG. 10, at least one knife 29 may extend from the anvil 32 of the end effector 4, facing toward the staple holder 30. As another example, at least one knife 29 may extend from the staple holder 30 toward the anvil 32. As another example, two knives 29 may be provided, one extending from the staple holder 30 and one extending from the anvil 32, where both are oriented and positioned relative to one another such that the knives 29 move together as the end effector 4 moves from an open configuration to a closed configuration. At least one knife 29 may be fixed directly to the anvil 32 or to the staple holder 30, depending on the particular configuration of the end effector 4. As another example, at least one knife 29 may extend from and be movable relative to the staple holder 30 and/or the anvil 32. In this situation, as one example, the knife 29 may be fabricated from spring steel or similar material, which is held in a channel defined in the corresponding staple holder 30 or anvil 32. The knife 29 may be actuated before, during or after closure of the end effector 4 to move along and/or out of the corresponding channel.

Figure 11:
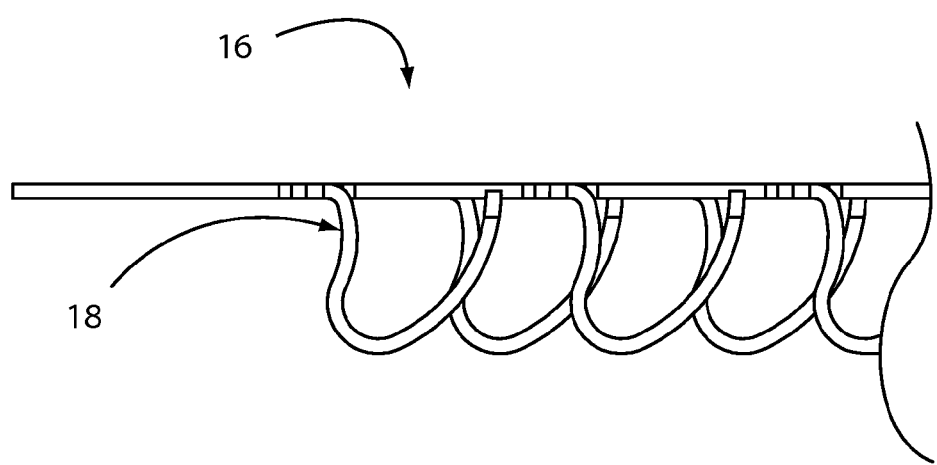
FIG. 11 is a side view of another exemplary feeder belt.

Referring also to FIG. 11, the nose or pulley disclosed in the Endocutter Applications optionally may be omitted where the feeder belt 16 is deployed in addition to the staples 18 attached to it. Concurrently, the lower section of the feeder belt 16 may be omitted, because the feeder belt 16 need not wrap around the nose or pulley where the distalmost section of the feeder belt 16 is separated from a remainder of the feeder belt 16 after each deployment of staples 18. As a result, the feeder belt 16 may be advanced generally linearly without substantially bending, and the feeder belt 16 may be generally straight and lie substantially in a single plane. Consequently, the choice of materials from which the feeder belt 16 may be fabricated may expand, because the feeder belt 16 need not be flexible enough to wrap around a nose or pulley.

Figure 12:
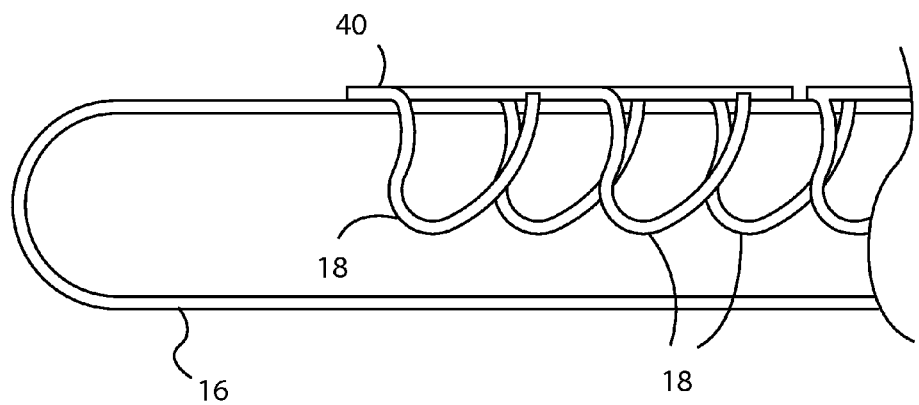
FIG. 12 is a side view of another exemplary feeder belt, to which at least one detachable carrier is connected.
Figure 13:
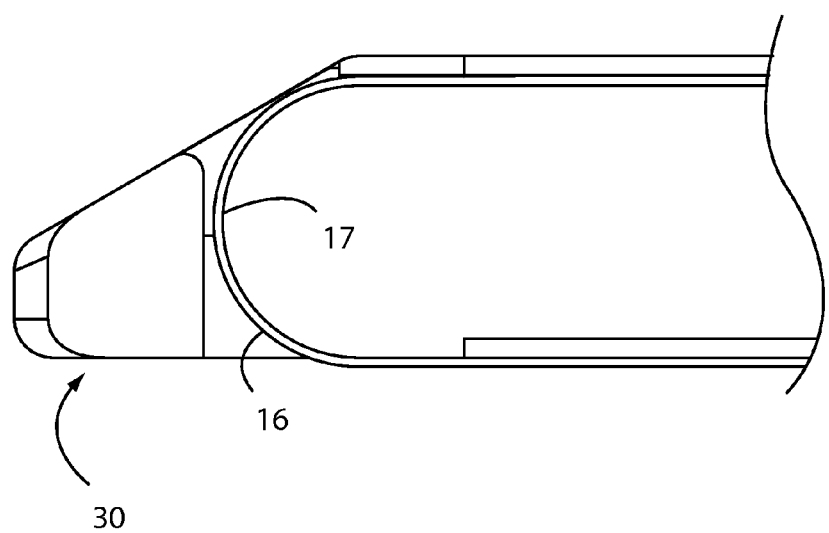
FIG. 13 is a detail cross-section view of the staple holder.

In another exemplary embodiment, referring also to FIG. 12, at least one resorbable carrier 40 may be detachably held on a feeder belt 16, where the staples 18 are fixed to the carrier 40 rather than the feeder belt 16. The feeder belt 16 may wrap around a nose, pulley or other structure at its distal end, such as described in the Endocutter Applications. Referring also to FIG. 13, the term "redirector" 17 is defined to include a nose, a pulley or any other structure or mechanism about which the distal end of the feeder belt 16 wraps or extends. In such an embodiment, the feeder belt 16 simply may urge the carrier or carriers 40 distally, and may not include staples 18 extending therefrom. Each carrier 40 may be held on an upper surface of the corresponding feeder belt 16 in order to facilitate deployment of the carrier 40 out of the staple holder 30. That is, each carrier 40 may be located between the corresponding feeder belt 16 and the aperture, slot or other opening in the upper surface of the staple holder 30 through which the carrier 40 is to be deployed. Alternately, at least one carrier 40 may extend at least partially underneath the corresponding feeder belt 16. Each carrier 40 may be held by the feeder belt 16 in any suitable manner. As one example, adhesive may connect a carrier 40 to the corresponding feeder belt 16. As another example, at least one carrier 40 may be frangibly connected to the corresponding feeder belt 16. As another example, at least one carrier 40 may be pressure fit or interference fit onto the corresponding feeder belt 16. As another example, at least one carrier 40 may be snap fit onto a corresponding feeder belt 16 such as via a tab extending from the carried 40 into a slot on the feeder belt 16, or vice versa. The carriers 40 may be independent from one another, and independently held by the corresponding feeder belt 16. Alternately, at least two carriers 40 may be connected directly to one another, such that a connection between two adjacent carriers 40 is severed during deployment of the most-distal carrier 40. Such connection and severing may be, for example, as set forth above with regard to the embodiment of FIGS. 9-11. As another example of a carrier 40, the staples 18 may be resorbable as well as the carrier 40. As another example, the carrier 40 may be non-resorbable, as well as the staples 18 attached thereto.

Operation

Operation of the endocutter 2 is substantially as described in the Endocutter Applications. For clarity and brevity, the differences between that operation described in the Endocutter Applications and the operation of the end effector 4 of this document are described here. The end effector 4 is placed in proximity to tissue to be treated, whether in a conventional or minimally-invasive surgical procedure. At such time, if the end effector 4 is in the closed configuration, it is then moved to the open configuration. The end effector 4 is then moved to the closed configuration such that the tissue to be treated is positioned between the staple holder 30 and the anvil 32. The end effector 4 is then actuated, such as by depressing a firing trigger on the handle 8, as described in the Endocutter Applications.

Where at least one knife 29 is fixed to the anvil 32, as the end effector 4 moves from an open configuration to a closed configuration, at least one knife 29 may encounter and then cut through at least one feeder belt 16. Advantageously, that knife 29 encounters and cuts through at least one feeder belt 16 at a perforation 24. The staple holder 30 may include an aperture defined therein through which the knife 29 is received, in order to allow the knife 29 to make contact with at least one feeder belt 16. That aperture may be independent from one or more apertures in the staple holder 30 through which the staples 18 are deployed, or may be a larger slot through which at least one staple 18 is deployed. Where at least one knife 29 is fixed to the staple holder 30 under a corresponding feeder belt 16, the anvil 32 may be configured to press against the feeder belt 16 at a location above the knife 29, such that the resulting pressure causes the knife 28 to cut through the feeder belt 16. Where at least one knife 29 is fixed to the anvil 32 and/or staple holder 30, that knife 29 cuts through one or more feeder belts 16 during closure of the end effector 4. Thus, the most-distal section of at least one feeder belt 16 is separated from a proximal remainder of the feeder belt 16 during closure of the end effector 4. That distalmost section of the feeder belt 16 may be held within the staple holder 30 in any suitable manner, such as by a clamping force exerted by the anvil 32 against the staple holder 30, by clamps within the staple holder 30 such as described in the Endocutter Applications, by pressure or interference fit between the feeder belt 16 and the staple holder 30, or by any other suitable structure or method. The staples 18 are then deployed such as described in the Endocutter Applications. After the staples 18 have been deployed, the staples 18 hold the separated portion of the feeder belt 16 in place relative to the tissue that was stapled. The feeder belt 16 is unclamped, and the separated portion of that feeder belt 16 is then free to exit the staple holder 30 as the staple holder 30 is moved away from tissue, such that the separated portion of the feeder belt 16 is passively ejected from the staple holder 30. Alternately, the separated portion of the feeder belt 16 may be actively ejected from the staple holder 30 in any suitable manner.

Where at least one knife 29 is movable relative to the staple holder 30 and/or the anvil 32, the end effector 4 can be moved to the closed configuration without simultaneously cutting at least one feeder belt 16. Consequently, at least one knife 29 can be actuated after the end effector 4 has moved to the closed configuration. Advantageously, that knife 29 encounters and cuts through at least one feeder belt 16 at a perforation 24. As one example, the staples 18 may be deployed such as described in the Endocutter Applications, and at least one knife 29 may then be actuated to contact and then cut through a corresponding feeder belt 16, separating the most distal part of that feeder belt 16 from a remainder of that feeder belt 16. As another example, at least one knife 29 may be actuated to contact and then cut through a corresponding feeder belt 16, separating the most distal part of that feeder belt 16 from a remainder of that feeder belt 16, and then the staples 18 connected to that separated portion of the feeder belt 16 may be deployed such as described in the Endocutter Applications. As described in the Endocutter Applications, regardless of the timing of the actuation of the knife 29 to cut through a corresponding feeder belt 16, that feeder belt 16 may be clamped securely relative to the staple holder 30 during deployment of the staples 18. After the staples 18 have been deployed, the staples 18 hold the separated portion of the feeder belt 16 in place relative to the tissue that was stapled. The feeder belt 16 is unclamped, and the separated portion of that feeder belt 16 is then free to exit the staple holder 30 as the staple holder 30 is moved away from tissue, such that the separated portion of the feeder belt 16 is passively ejected from the staple holder 30. Alternately, the separated portion of the feeder belt 16 may be actively ejected from the staple holder 30 in any suitable manner.

As another example, the knife 29 may be omitted. If so, the feeder belt 16 may include at least one perforation 24, where that perforation 24 is strong enough in compression to allow the feeder belt 16 to be advanced relative to the staple holder 30, and weak enough to allow the distalmost portion of the feeder belt 16 to separate easily from a remainder of the feeder belt 16. If so, the feeder belt 16 may be clamped into place relative to the staple holder 30, along a length that extends proximal to the most-distal perforation 24. The staples 18 are then deployed into tissue, and then the feeder belt 16 is unclamped. The staple holder 30 is then moved away from the tissue into which the staples 18 were deployed, such that a tensile force is applied to the portion of the feeder belt 16 distal to the most distal perforation 24. That tension causes the distalmost section of the feeder belt 16 to tear away at the perforation 24, leaving that distalmost section of the feeder belt 16 within the patient.

As another example, where at least one carrier 40 is detachably held on a feeder belt 16, at least one carrier 40 may be independent from adjacent carriers. The term "independent" means that a carrier 40 is not directly connected to any adjacent carrier 40. The feeder belt 16 optionally may be clamped in place, and then the staples 18 are deployed, such as described in the Endocutter Applications. After the staples 18 have been deployed into tissue, the staple holder 30 is moved away from the tissue. This motion exerts a force on the carrier 40, detaching it from the corresponding feeder belt 16. Alternately, the carrier 40 may be actively ejected from the corresponding feeder belt 16 in any suitable manner. Where the carrier 40 is connected to another carrier 40, the knife 29 may be utilized as described above to sever the distalmost carrier 40 from the carrier 40 located proximal to it. The knife 29 may separate the distalmost carrier 40 during closure of the end effector 4, or after the end effector 4 has been closed, as described above.

In each example above, the feeder belt 16 may be advanced after each deployment, without the need to remove the end effector 4 from the patient, such that true multi-fire capability is provided.

The resorbable material left in the patient degrades over time. Where the feeder belt 16 or carrier 40 left within the patient is resorbable, and the staples 18 are not, the staples 18 remain in place in the patient after the feeder belt 16 or carrier 40 have degraded. Where the staples 18 are resorbable as well, the staples 18 degrade along with the feeder belt 16 or carrier 40. Complete resorbability may be desirable where the tissue to be treated is expected to heal quickly, and where the use of permanently-implanted staples 18 is not advantageous.

Where neither the staples 18 nor the feeder belt 16 or carrier 40 are resorbable, then they remain in place in the patient at the treatment site. Permanent implantation may be desirable where the tissue to be treated is expected to heal slowly or not at all, and where the use of permanently-implanted staples 18 is advantageous.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
   a single resorbable feeder belt; and
   a plurality of staples each having a first leg terminating at a first end and a second leg terminating at a second end, wherein each staple has an open perimeter prior to deployment, the open perimeter defined between the first end and the second end, and wherein the first end of each staple of the plurality of staples is fixed to said single resorbable feeder belt at a location that remains constant throughout staple formation prior to separation from said feeder belt.

2. The surgical apparatus of claim 1, wherein at least one of said staples is resorbable.

3. The surgical apparatus of claim 1, further comprising at least one perforation defined in said feeder belt.

4. The surgical apparatus of claim 1, further comprising an end effector including an anvil and a staple holder pivotally connected to one another, wherein said anvil holds a knife, and wherein said feeder belt extends into said staple holder.

5. The surgical apparatus of claim 4, wherein said knife is configured to cut through said feeder belt.

6. The surgical apparatus of claim 4, wherein said knife is fixed to said anvil.

7. The surgical apparatus of claim 4, wherein said knife is movable along a channel defined in said anvil.

8. The surgical apparatus of claim 1, wherein said feeder belt lies substantially in a single plane.

9. The surgical apparatus of claim 1, further comprising an end effector including an anvil and a staple holder pivotally connected to one another, wherein said staple holder holds a knife.

10. The surgical apparatus of claim 1, wherein each staple of the plurality of staples rotates around respective first end during staple formation.

11. The surgical apparatus of claim 1, wherein the feeder belt is configured as a loop.

12. The surgical apparatus of claim 1, wherein the second end of each staple of the plurality of staples is below a plane of a top surface of the feeder belt.

13. Surgical apparatus, comprising:
a contiguous feeder belt; and
a resorbable carrier detachably connected to said feeder belt, wherein said carrier includes a plurality of staples affixed thereto;
wherein each said staple has a first leg terminating at a first end and a second leg terminating at a second end, thereby defining an open perimeter between ends of the first leg and the second leg prior to deployment, and wherein the first end of each staple is fixed to the carrier at a location that remains constant throughout staple formation.

14. The surgical apparatus of claim 13, wherein the carrier is detachably connected to an upper surface of said feeder belt.

15. The surgical apparatus of claim 13, wherein a plurality of carriers are detachably connected to the feeder belt, and wherein said plurality of carriers are independent from one another.

16. The surgical apparatus of claim 13, further comprising a staple holder into which the feeder belt extends; wherein said staple holder includes at least one redirector about which the distal end of said feeder belt extends.

17. The surgical apparatus of claim 16, wherein said feeder belt is retained within staple holder during detachment of said at least one carrier.

18. The surgical apparatus of claim 13, wherein each staple rotates around respective first end during staple formation.

19. The surgical apparatus of claim 13, wherein the second end of each staple of the plurality of staples is below a plane of a top surface of the feeder belt.

* * * * *